United States Patent
Fan et al.

(10) Patent No.: US 12,115,221 B2
(45) Date of Patent: Oct. 15, 2024

(54) PICKERING EMULSION STABILIZED BY CELLULOSE NANOCRYSTALS FROM GINKGO SEED SHELLS AND PREPARATION METHOD THEREOF

(71) Applicant: Jiangnan University, Wuxi (CN)

(72) Inventors: Liuping Fan, Wuxi (CN); Yang Ni, Wuxi (CN); Jinwei Li, Wuxi (CN)

(73) Assignee: Jiangnam University, Wuxi (CN)

( * ) Notice: Subject to any disclaimer, the term of this patent is extended or adjusted under 35 U.S.C. 154(b) by 870 days.

(21) Appl. No.: 17/216,771

(22) Filed: Mar. 30, 2021

(65) Prior Publication Data
US 2021/0213405 A1 Jul. 15, 2021

Related U.S. Application Data

(63) Continuation of application No. PCT/CN2019/130267, filed on Dec. 31, 2019.

(30) Foreign Application Priority Data

Oct. 31, 2019 (CN) .......................... 201911050938.3

(51) Int. Cl.
*A61K 47/38* (2006.01)
*A23D 7/005* (2006.01)
(Continued)

(52) U.S. Cl.
CPC ............ *A61K 47/38* (2013.01); *A23D 7/0053* (2013.01); *A23D 7/04* (2013.01); *A23G 9/327* (2013.01);
(Continued)

(58) Field of Classification Search
CPC ................................. A61K 47/38; A61K 8/06
See application file for complete search history.

(56) References Cited

U.S. PATENT DOCUMENTS

| | | | | |
|---|---|---|---|---|
| 2013/0122071 A1* | 5/2013 | Cathala | ..................... | C08F 4/12 424/401 |
| 2014/0073706 A1* | 3/2014 | Capron | ..................... | C08L 1/04 252/62 |

(Continued)

FOREIGN PATENT DOCUMENTS

| | | |
|---|---|---|
| CN | 102553470 A | 7/2012 |
| CN | 108350653 A | 7/2018 |
| CN | 108892787 A | 11/2018 |

*Primary Examiner* — Jonathan M Hurst
(74) *Attorney, Agent, or Firm* — IPRO, PLLC (57) ABSTRACT

The disclosure discloses a Pickering emulsion stabilized by cellulose from ginkgo seed shells and a preparation method thereof, and belongs to the fields of preparation methods of biomass materials and food chemical industry. The disclosure uses ginkgo seed shells as a raw material to obtain high-purity cellulose through hot alkali treatment and sodium chlorite bleaching. After the cellulose is dried, the cellulose is hydrolyzed with sulfuric acid to obtain a cellulose nanocrystal suspension. The suspension is mixed with an oil phase, and the Pickering emulsion is obtained through high-speed shearing and homogeneous emulsification. The disclosure can prepare cellulose nanocrystals with different aspect ratios by adjusting the parameters of high-speed shearing and homogeneous emulsification according to actual production needs. Cellulose nanocrystals with high aspect ratio can be used to prepare stable Pickering emulsions with high oil phase and high viscosity, which can be applied to the fields of food, cosmetics and the like; and cellulose nanocrystals with low aspect ratio can be used to prepare Pickering emulsions with low viscosity and high fluidity, which can to be applied to the fields of food and medicine.

18 Claims, 5 Drawing Sheets

(51) Int. Cl.
*A23D 7/04* (2006.01)
*A23G 9/32* (2006.01)
*A61K 9/107* (2006.01)
*C08B 1/00* (2006.01)
*C08B 15/08* (2006.01)
*C09K 23/00* (2022.01)
*C09K 23/56* (2022.01)

(52) U.S. Cl.
CPC ............ *A61K 9/1075* (2013.01); *C08B 1/003* (2013.01); *C08B 15/08* (2013.01); *C09K 23/00* (2022.01); *C09K 23/56* (2022.01); *A23V 2002/00* (2013.01)

(56) References Cited

U.S. PATENT DOCUMENTS

| | | | | |
|---|---|---|---|---|
| 2015/0368367 | A1* | 12/2015 | Hu | C08B 15/08 106/501.1 |
| 2019/0360151 | A1* | 11/2019 | Hamad | D21C 3/00 |
| 2021/0144993 | A1* | 5/2021 | Kim | A61K 47/44 |

* cited by examiner

PICKERING EMULSION STABILIZED BY CELLULOSE NANOCRYSTALS FROM GINKGO SEED SHELLS AND PREPARATION METHOD THEREOF

TECHNICAL FIELD

The disclosure relates to a Pickering emulsion stabilized by cellulose from ginkgo seed shells and a preparation method thereof, and belongs to the fields of preparation methods of biomass materials and food chemical industry.

BACKGROUND

Traditional emulsions are stabilized by small-molecule surfactants, which is a meta-stable system dynamically stable but thermodynamically unstable. Compared with traditional emulsions, Pickering emulsions have better stability, anti-aggregation, anti-flocculation and anti-Austenitic abilities. This is because solid particles playing an emulsifying effect in the emulsion are irreversibly adsorbed on a water-oil interface, which not only reduces the total free energy of a system, but also provides a spatial physical barrier for the contact between droplets. The solid particles even form a three-dimensional network structure in a dispersed phase, which gives the Pickering emulsions stronger stability. In recent years, as consumers have gradually increased their attention to "green food" and "clean label", compared with the traditional emulsions stabilized by synthetic small molecule emulsifiers, Pickering emulsions stabilized by biological materials has better safety and environmental compatibility. Therefore, Pickering emulsions have broad application prospects in the fields of cosmetics, medicine and food.

At present, the research on application of inorganic particles in Pickering emulsions is relatively more and mature, but the inorganic particles are potentially harmful to the human body. Food-grade biomass materials such as starch, protein and cellulose have the characteristics of good biocompatibility, wide range of sources and renewability, and have attracted the attention of a large number of researchers. Among them, as one of the most commonly used biopolymers, cellulose has become a good candidate for food-grade Pickering emulsion stabilizers due to its abundant source, low cost, biodegradability and biocompatibility. The excellent properties of Pickering emulsions make their application in the food industry have broad prospects, but the morphology of cellulose nanocrystals significantly affects the properties of the emulsion. The aspect ratio is an important indicator of the morphology of cellulose nanocrystals. Cellulose nanocrystals with low aspect ratio can be used to prepare Pickering emulsions with low viscosity and better fluidity, which can be used for coating and delivery of biologically active substances. Cellulose crystals with high aspect ratio can be used to stabilize Pickering emulsions with 70% or more oil phase, and can replace partial hydrogenated vegetable oil to be applied in foods to prepare products such as cream, ice cream, mayonnaise and the like. Although many documents and patents have reported the use of different biomass cellulose raw materials to prepare CNCs (cellulose nanocrystals), these CNCs have different lengths, widths, and aspect ratios due to different raw materials and hydrolysis processes. However, in most of the CNCs reported in the literature and patents, generally only CNCs with one aspect ratio are obtained under the preparation process conditions.

For example, in a Chinese Invention patent of "Pickering Emulsion Prepared from Palm Empty Fruit Bunches as Cellulose Raw Material and Preparation Method thereof" (CN108892787A) similar to the disclosure, palm empty fruits are used as a raw material and cooked by a soda process; then, after a series of 0-D1-E0P-D2 bleaching and hydrolyzing with sulfuric acid, nano-cellulose crystals are obtained; then the obtained nano-cellulose crystals are used as a solid particle emulsifier to be mixed with an oil phase; and the Pickering emulsion is prepared by emulsification. However, the soda cooking process in the invention patent has long heating time and the operative temperature reaches 160-180° C., so that the energy consumption is high; the bleaching process has four steps, and is very complicated; and finally single mercerized nanocellulose crystals are obtained. In addition, the oil phase used in the emulsion is chemical reagents such as dichloromethane, trichloroethylene, toluene and n-hexadecane, which cannot be used in the food field. The highest oil-water ratio of the emulsion in the patent is 4:6, which is lower than the highest oil-water ratio of 8:2 of the disclosure.

The SCI article "Production of cellulose nanocrystals from pistachio shells and their application for stabilizing Pickering emulsions" similar to the disclosure uses pistachio shells as raw materials to prepare CNCs by acid hydrolysis. Although the pretreatment of the raw materials and the hydrolysis process are similar, the obtained CNCs have only one size, while the disclosure herein can obtain CNCs with different aspect ratios through subsequent high-pressure homogenization treatment. CNCs can be used as nanocomposite material performance modifiers and emulsion stabilizers. The morphologies and properties of CNCs will affect their performance as modifiers and stabilizers. Compared with CNCs of a single size, the method of the disclosure can adjust the size of CNCs according to actual effects, so as to better improve nanomaterials and stabilize emulsions. In addition, the highest oil-water ratio of the emulsion in the article as described above is 1:9, which is lower than the highest oil-water ratio of 8:2 of the disclosure.

SUMMARY

The objective of the disclosure is to provide a method for preparing cellulose nanocrystals with different aspect ratios and application thereof in Pickering emulsions. The method of the disclosure includes: firstly, cellulose from gingko seed shells is purified by alkali treatment and rinsing treatment, then the amorphous region of the cellulose is removed by sulfuric acid hydrolysis, an aggregated cellulose microcrystal suspension is obtained by dialysis, and after the cellulose microcrystal suspension is subjected to high-pressure homogenization treatment, cellulose nanocrystals with different aspect ratios are obtained; and then the cellulose nanocrystals are used as emulsion stabilizers to prepare Pickering emulsions.

The disclosure provides a Pickering emulsion stabilized by cellulose from ginkgo seed shells and a preparation method thereof, and the method includes the following steps:

(1) crushed ginkgo seed shells are treated with a hot alkali solution, then rinsed with a rinsing solution, and dried with hot air to obtain high-purity cellulose from ginkgo seed shells;

(2) the cellulose from ginkgo seed shells obtained in step (1) is hydrolyzed with sulfuric acid; after the hydrolysis, deionized water is added immediately to terminate the reaction; the hydrolysate is centrifuged to obtain a precipitate; the precipitate is dialyzed with deionized water to remove inorganic salt ions; and a cellulose microcrystal suspension is obtained after dialysis;

(3) the cellulose suspension obtained in step (2) is homogenized, and cellulose nanocrystals with different aspect ratios are prepared by adjusting the homogenization pressure; and (4) the cellulose nanocrystals in step (3) are used as a solid particle emulsifier, mixed with an oil phase, and then emulsified to obtain the Pickering emulsion.

In one example, the method includes the following specific steps:

(1) Purification of cellulose from ginkgo seed shells: crushed ginkgo seed shells are mixed with a preheated 2-5 wt % sodium hydroxide solution in a material-liquid ratio of 1:20 to 1:40 (w/v); then the mixture is heated in a water bath at 80-100° C. for 1-3 h, filtered, washed with deionized water 2-4 times, and dried with hot air at 40-60° C.; the dried cellulose is mixed with a rinsing solution in a material-liquid ratio of 1:20 to 1:50 (w/v); the mixture is heated in a water bath at 80-100° C. for 1-3 h; then the mixture is filtered to remove the rinsing solution, and dried with hot air at 40-60° C.

(2) Preparation of CNCs (cellulose nanocrystals): the dry cellulose powder obtained in step (1) is mixed with a preheated sulfuric acid solution with the mass concentration of 58-64% for hydrolysis reaction, wherein the hydrolysis temperature is 40-50° C., the hydrolysis reaction time is 10-60 min, and the material-liquid ratio of the cellulose to the sulfuric acid solution is 1:10 to 1:20 (w/v); after the hydrolysis, the reaction is immediately terminated with 10-15 times of deionized water by volume; then centrifugation is carried out to remove the sulfuric acid hydrolysate; the centrifuged precipitate is redispersed into deionized water to obtain a suspension; a dialysis bag is filled with the suspension; and dialysis is repeated with deionized water until the pH of the suspension is stable, so as to obtain a cellulose microcrystal suspension.

(3) Preparation of cellulose nanocrystals with different aspect ratios: the cellulose suspension obtained in step (2) is homogenized, wherein the homogenization pressure is 10-100 MPa, the number of cycles is 4, and the homogenization temperature is room temperature; CNCs with high aspect ratio are obtained by homogenization treatment at the pressure of 10-30 MPa; and CNCs with low aspect ratio are obtained by homogenization treatment at the pressure of 30-100 MPa.

(4) Preparation of the Pickering emulsion: the cellulose nanocrystals in step (3) used as a solid particle emulsifier are mixed with an oil phase, and emulsification is carried out to obtain the Pickering emulsion.

In one example, the rinsing solution in step (1) of the method is that 100 mL of rinsing solution contains 1.5-2.0 g of sodium chlorite, 2.5-3.0 g of sodium hydroxide and 7-8 mL of glacial acetic acid.

In one example, the molecular weight cut-off of the dialysis bag in step (2) of the method is 8-14 kDa.

In one example, the centrifugation conditions in step (2) of the method are: the rotation speed is 7000-8000 rpm, the centrifugation temperature is 15° C., and the centrifugation time is 15-20 min.

In one example, the oil phase in step (4) of the method is edible oil such as corn oil, soybean oil, and peanut oil; and the concentration of cellulose nanocrystals in a water phase is 0.10-0.50 wt %.

In one example, in step (4) of the method, a certain amount of cellulose nanocrystals with high aspect ratio are mixed with 50%-80% of oil phase, and emulsification is carried out to obtain a Pickering emulsion with high oil phase and high viscosity.

In one example, in step (4) of the method, a certain amount of cellulose nanocrystals with low aspect ratio are mixed with 10%-50% of oil phase, and emulsification is carried out to obtain a Pickering emulsion with low viscosity and high fluidity.

In one example, the emulsification method in step (4) of the method includes high-speed shearing, homogenization, or a combination of high-speed shearing and homogenization, wherein the high-speed shearing conditions are: the shearing rate is 8000-10000 rpm, the shearing time is 1-3 min; and the homogenization process is: the homogenization pressure is 10-30 MPa, the number of cycles is 2-6, and the temperature is controlled at 25° C.

In one example, the Pickering emulsion stabilized by cellulose from ginkgo seed shells can be applied to the fields of food, cosmetics and the like.

In one example, the Pickering emulsion stabilized by cellulose from ginkgo seed shells can be applied to the field of delivery of biologically active substances.

Beneficial Effects of the Disclosure (1) The disclosure can prepare high-purity and high-crystallized cellulose nanocrystals with the aspect ratio of 8-50. The process is simple, and reuse of agricultural and forestry waste is realized.

(2) The disclosure can select cellulose nanocrystals with different aspect ratios according to actual production needs: cellulose nanocrystals with high aspect ratio can be used to prepare stable Pickering emulsions with high oil phase and high viscosity, which can be applied to the fields of food, cosmetics and the like, and specifically can be applied to ice cream, emulsions and the like; and cellulose nanocrystals with low aspect ratio can be used to prepare Pickering emulsions with low viscosity and high fluidity, which can be applied to the fields of food and medicine, and specifically can be applied to the delivery of biologically active substances.

(3) The oil phase of the Pickering emulsions prepared by the disclosure is edible oil such as corn oil, soybean oil and peanut oil, the Pickering emulsions can be applied to the field of food, and the amount of the oil phase used is wide. When the amount of the oil phase used is 10%-80% of the emulsion, a stable Pickering emulsion can be formed, and the amount of cellulose used is small, only 0.10-0.50 wt % of the water phase.

(4) The emulsions prepared by the disclosure have good storage stability, and remain stable after being placed in the room temperature environment for 3 months. When the emulsions of the disclosure are placed in an environment with the pH of 2.5-9.5 and the ionic strength of 10-100 mM, the emulsion has no demulsification phenomenon. At the same time, no demulsification phenomenon occurs when the emulsion is heated to 90° C.

DETAILED DESCRIPTION

The disclosure will be further described in detail below in conjunction with specific examples, but the implementation of the disclosure is not limited to the examples.

Yield calculation formula: Yield (%)=$m_2 v_1/m_1 v_2 \times 100$, $m_1$ is the mass of cellulose after rinsing, $m_2$ is the mass of dry CNCs, $v_1$ and $v_2$ are respectively the total CNCs suspension volume and dry CNCs suspension volume obtained by hydrolysis.

Example 1 Preparation of Cellulose Nanocrystals with High Aspect Ratio and Pickering Emulsion Crushed ginkgo seed shells were mixed with a preheated 4 wt % sodium hydroxide solution in a material-liquid ratio of 1:20 (w/v), and then the mixture was heated in a water bath at 90° C. for 2 h, filtered, washed with deionized water 4 times, and then dried with hot air at 50° C. The dried cellulose was mixed with a rinsing solution in a material-liquid ratio of 1:30 (w/v), and the mixture was heated in a water bath at 80° C. for 2 h. Then the mixture was filtered to remove the rinsing solution, and dried with hot air at 50° C.

The dry cellulose powder was mixed with a preheated sulfuric acid solution with the mass concentration of 64% for hydrolysis reaction, wherein the hydrolysis temperature was 45° C., the hydrolysis reaction time was 30 min, and the material-liquid ratio of the cellulose to the sulfuric acid solution was 1:15 (w/v). After the hydrolysis, the reaction was immediately terminated with 10 times of deionized water by volume. Then centrifugation was carried out to remove the sulfuric acid hydrolysate, and the centrifuged precipitate was redispersed into deionized water to obtain a suspension. A dialysis bag with the molecular weight cut-off of 8-14 kDa was filled with the suspension, and dialysis was repeated with deionized water until the pH of the suspension was stable, so as to obtain a cellulose nanocrystal suspension. The suspension was circulated 4 times by a high-pressure homogenizer at 30 MPa. The length and diameter of CNCs were measured using Zetasizer ZEN3600 and an atomic force microscope (AFM), and the aspect ratio of the cellulose nanocrystals was calculated. Cellulose nanocrystals with a high aspect ratio of 21 were obtained, and the calculated yield was 67%.

Figure 1:
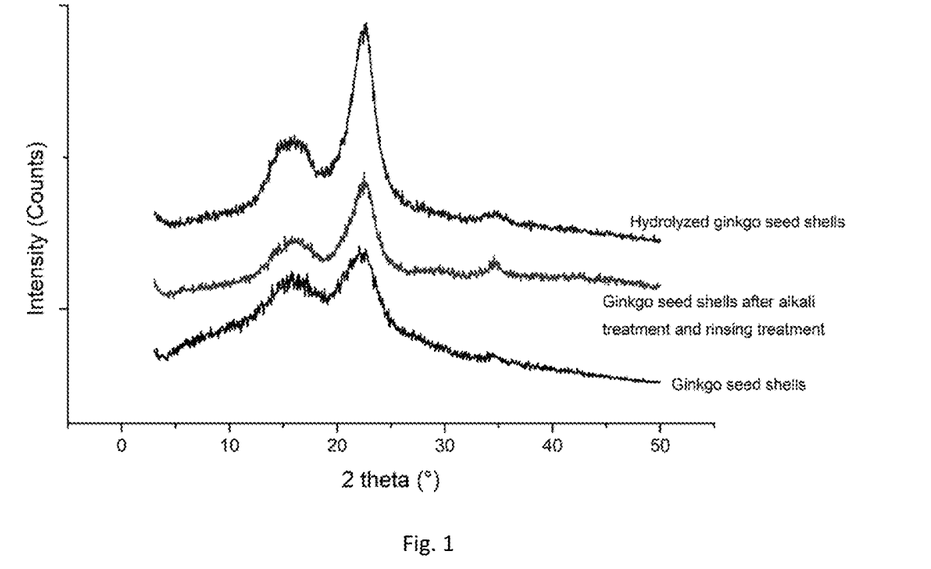
FIG. 1 shows the X-ray diffraction spectra of cellulose from ginkgo seed shells after different treatments.

XRD tests were carried out on the ginkgo seed shells, the ginkgo seed shells obtained after alkali treatment and rinsing, and the hydrolyzed ginkgo seed shells. FIG. 1 shows the XRD spectra of the cellulose from ginkgo seed shells after different treatments. It can be seen from FIG. 1 that after bleaching treatment and hydrolysis treatment, the XRD spectra of cellulose have a clear change, and the peak intensity increases significantly, which means that the crystallinity of the cellulose increases. This is because that the untreated cellulose contains a lot of impurities such as hemicellulose. After rinsing and bleaching, most of the hemicellulose can be removed, and then the amorphous regions in the cellulose are degraded by sulfuric acid hydrolysis, and thereby improving the crystallinity of the cellulose.

Figure 2:
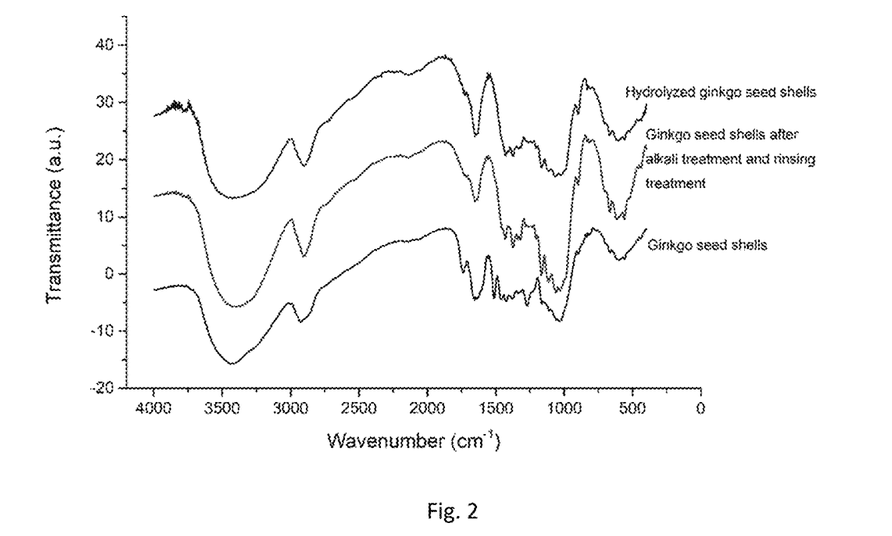
FIG. 2 shows the Fourier infrared spectra of cellulose from ginkgo seed shells after different treatments.

Fourier infrared tests were carried out on the ginkgo seed shells, the ginkgo seed shells obtained after alkali treatment and rinsing, and the hydrolyzed ginkgo seed shells. FIG. 2 shows the Fourier infrared spectra of the cellulose from ginkgo seed shells after different treatments. It can be seen from FIG. 2 that compared with the spectrum of the untreated ginkgo seed shells, the spectra of the ginkgo seed shells after alkali treatment and rinsing have certain changes, and the absorption peaks at 1735 $cm^{-1}$, 1500 $cm^{-1}$ and 1270 $cm^{-1}$ disappear. The absorption peak at 1735 $cm^{-1}$ is related to stretching of the C=O bonds in the carbonyl group, ester group and acetyl group in the xylan components of lignin and hemicellulose; the peak at 1500 $cm^{-1}$ is the C=C bond in the aromatic ring of lignin; and the peak at 1270 $cm^{-1}$ is related to stretching of the C—O in the aromatic group in lignin. The disappearance of the peaks means that after alkali treatment and rinsing, the hemicellulose and lignin in the ginkgo seed shells are basically removed. In addition, there is no significant difference between the spectrum of the ginkgo seed shells after the hydrolysis treatment and the spectrum of the ginkgo seed shells after the alkali treatment, which indicates that the hydrolysis did not produce new groups.

The cellulose crystal suspension was diluted to 0.1 wt %, and corn oil was added to the water phase according to the oil-water ratio of 5:5. Subsequently, high-speed shearing was carried out at 10000 rpm for 2 min using high-speed shearing equipment to obtain a coarse emulsion, and then the coarse emulsion was circulated 4 times at 30 MPa using a high-pressure homogenizer to obtain the final Pickering emulsion. The viscosity of the emulsion was 8.5 Pa·s. The obtained emulsion remained stable after being placed at room temperature for 3 months.

Example 2 Preparation of Cellulose Nanocrystals of Different Particle Sizes Under Different Homogenization Pressures Cellulose nanocrystals were prepared. The homogenization pressure on the cellulose nanocrystal suspension was changed on the basis of Example 1, and the cellulose nanocrystal suspension was homogenized 4 times repeatedly under 0 MPa, 10 MPa, 30 MPa, 50 MPa and 70 MPa respectively. Other preparation conditions were the same as in Example 1.

The length and diameter of CNCs under different homogenization pressures were measured using Zetasizer ZEN3600 and an atomic force microscope (AFM), and the aspect ratio of the cellulose nanocrystals was calculated. Table 1 shows the length, diameter and aspect ratio of the cellulose crystals treated under different homogenization pressures. It can be seen from Table 1 that as the homogenization pressure increases, the diameter is less affected, while the length of CNCs significantly decreases, and further causing the aspect ratio of CNCs to change from 51 to 8.

Figure 3A:
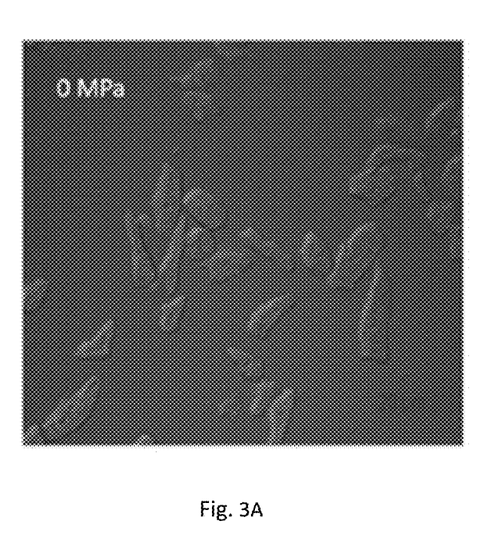
FIG. 3A is an optical microscope image of cellulose nanocrystals homogenized at 0 MPa.
Figure 3B:
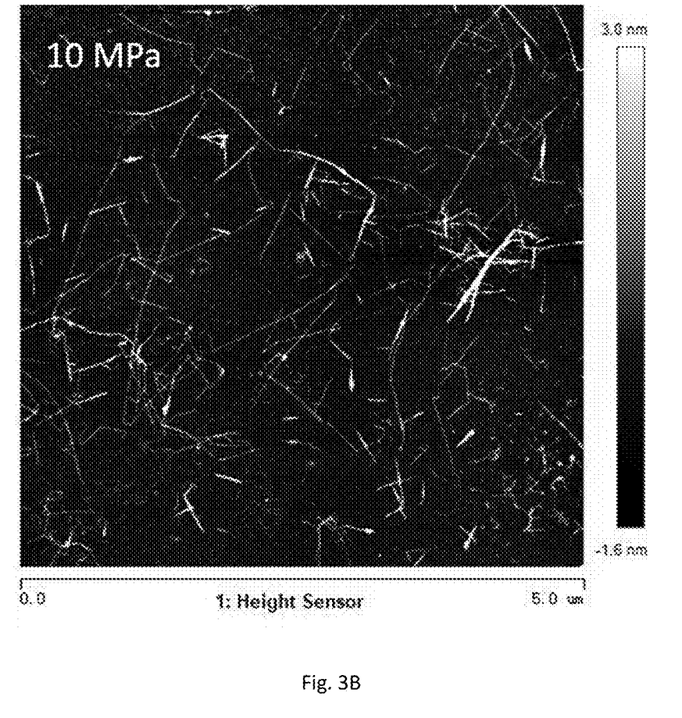
FIG. 3B is an AFM (Atomic Force Microscope) image of cellulose nanocrystals homogenized at 10 MPa.
Figure 3C:
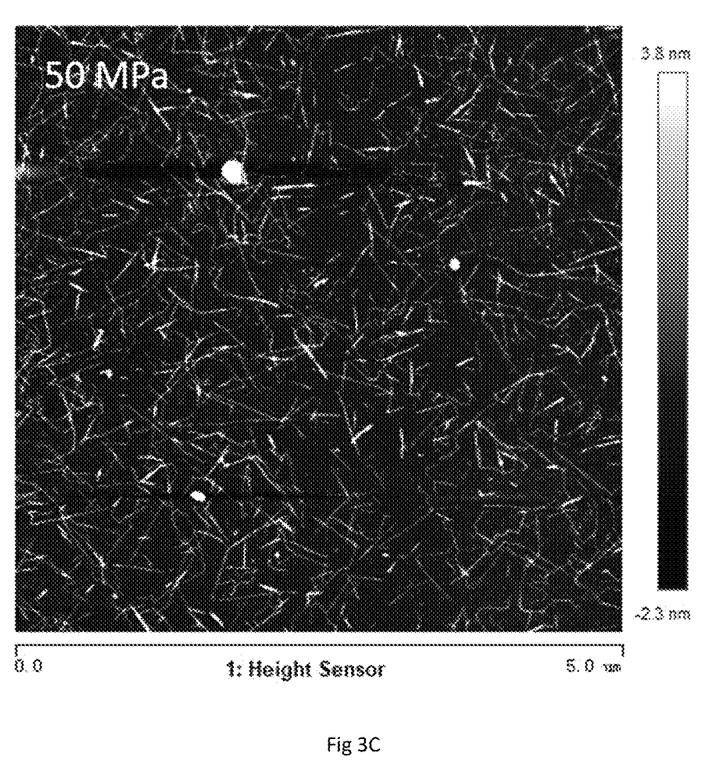
FIG. 3C is an AFM image of cellulose nanocrystals homogenized at 50 MPa.

Optical microscope images and atomic force microscope (AFM) images of cellulose nanocrystals homogenized at 0 MPa, 10 MPa and 50 MPa were taken respectively. FIG. 3A is an optical microscope image of cellulose nanocrystals homogenized at 0 MPa, FIG. 3B is an AFM image of cellulose nanocrystals homogenized at 10 MPa, and FIG. 3C is an AFM image of cellulose nanocrystals homogenized at 50 MPa. From FIG. 3B, it can be seen that the aggregated cellulose was dispersed by the 10 MPa homogenization process and formed an elongated noodle shape. As the homogenization pressure increases to 50 MPa (FIG. 3C), the elongated CNCs in FIG. 3B became rod-shaped CNCs.

TABLE 1

Length, diameter and aspect ratio of cellulose crystals subjected to homogenization treatment under different pressures

| Sample | Treatment condition | Length (nm) | Diameter (nm) | Aspect ratio |
|---|---|---|---|---|
| 1 | 0 MPa | / | $14212 + 1080^d$ | / |
| 2 | 10 MPa | $1500 + 248^d$ | $29.21 + 2.1^c$ | 51.72 |
| 3 | 30 MPa | $566 + 41^c$ | $27.21 + 1.8^b$ | 20.96 |
| 4 | 50 MPa | $344 + 20^b$ | $25.21 + 0.9^a$ | 13.76 |
| 5 | 70 MPa | $206 + 34^a$ | $24.21 + 2.0^a$ | 8.58 |

Example 3 Preparation of Cellulose Nanocrystals Under Different Hydrolysis Times Cellulose nanocrystals were prepared. The hydrolysis time was changed to 0 min, 10 min, 30 min, 60 min and 90 min on the basis of Example 1, and other preparation conditions were the same as in Example 1. After the reaction, the yield of CNCs was calculated. The yield of CNCs after 30 min of hydrolysis was 67%, the yield of CNCs after 60 min of hydrolysis was 50%, and the yield of CNCs after 90 min of hydrolysis was 42%.

Figure 4:
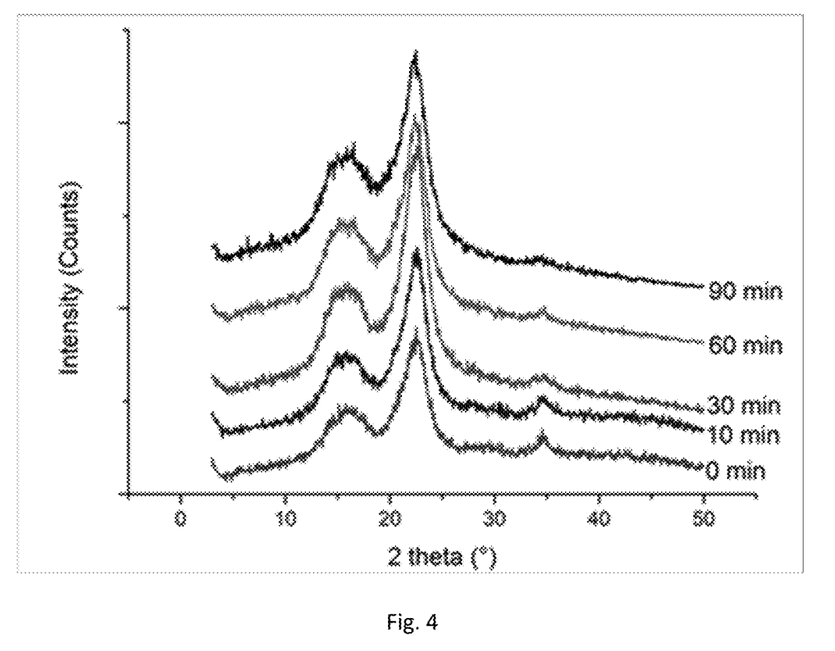
FIG. 4 shows the XRD spectra of cellulose from ginkgo seed shells hydrolyzed for different times.

FIG. 4 shows the XRD spectra of the cellulose from ginkgo seed shells with different hydrolysis times. It can be seen from FIG. 4 that when the hydrolysis time is 0 min, there are obvious peaks at 16.5°, 22.0° and 34.5°, which indicates that the cellulose from ginkgo seed shells is cellulose I. When the hydrolysis time increases to 30 min, the peak at 22.0° gradually increases. When the hydrolysis time exceeds 30 min, the peak at 22.0° decreases again, which indicates that during the hydrolysis time of 0-90 min, the crystallinity of CNCs firstly increases, reaches the maximum at 30 min, and then decreases. The decreased crystallinity indicates that part of the crystalline region in the cellulose was also degraded by sulfuric acid, which would lead to a decrease in the yield of cellulose.

Example 4 Pickering Emulsions Prepared by Cellulose Nanocrystals from Ginkgo Seed Shells with Different Concentrations The cellulose nanocrystals prepared in Example 1 were taken. The cellulose crystal suspension was diluted to 0.05 wt %, 0.1 wt %, 0.25 wt %, 0.35 wt % and 0.5 wt % respectively. Corn oil was added to the water phase according to the oil-water ratio of 5:5. Subsequently, high-speed shearing was carried out at 10000 rpm for 2 min using high-speed shearing equipment to obtain a coarse emulsion. Then the coarse emulsion was circulated 4 times at 30 MPa using a high-pressure homogenizer to obtain the final Pickering emulsion.

Figure 5:
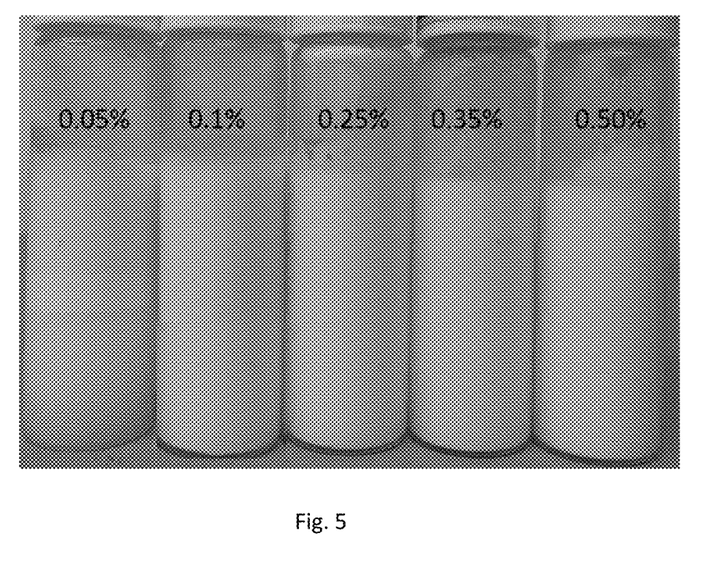
FIG. 5 shows the Pickering emulsions stabilized by cellulose nanocrystals from ginkgo seed shells with different concentrations.

FIG. 5 shows the Pickering emulsions stabilized by cellulose nanocrystals from ginkgo seed shells with different concentrations. It can be seen from FIG. 5 that the Pickering emulsions stabilized by CNCs are milky white. When the CNCs concentration is 0.05%, the emulsion is unstable. However, as the CNCs concentration increases to 0.1 wt %, the emulsion can be placed for 3 months without layering.

Figure 6:
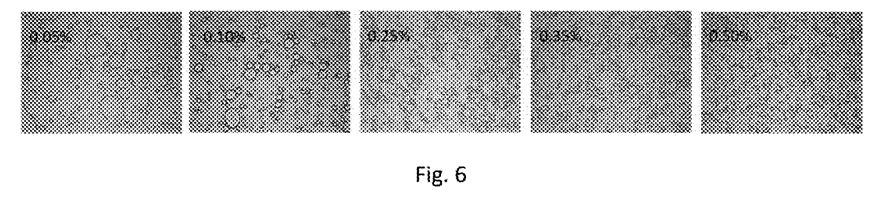
FIG. 6 is an optical micrograph of Pickering emulsions stabilized by cellulose nanocrystals from ginkgo seed shells with different concentrations.

FIG. 6 is an optical micrograph of Pickering emulsions stabilized by cellulose nanocrystals from ginkgo seed shells with different concentrations. It can be seen from FIG. 6 that as the concentration of CNCs increases, the size of emulsion droplets gradually decreases and the emulsion droplets are evenly distributed in the field of view, which indicates that the cellulose is uniformly adsorbed on the interface of the emulsion droplets and plays a good role in protecting the emulsion.

Example 5 Preparation of Cellulose Nanocrystals with High Aspect Ratio and Pickering Emulsion Crushed ginkgo seed shells were mixed with a preheated 2 wt % sodium hydroxide solution in a material-liquid ratio of 1:30 (w/v), and then the mixture was heated in a water bath at 90° C. for 2 h, filtered, washed with deionized water 4 times, and then dried with hot air at 50° C. The dried cellulose was mixed with a rinsing solution in a material-liquid ratio of 1:25 (w/v), and the mixture was heated in a water bath at 80° C. for 2 h. Then the mixture was filtered to remove the rinsing solution, and dried with hot air at 50° C.

The dry cellulose powder was mixed with a preheated sulfuric acid solution with the mass concentration of 60% for hydrolysis reaction, wherein the hydrolysis temperature was 50° C., the hydrolysis reaction time was 60 min, and the material-liquid ratio of the cellulose to the sulfuric acid solution was 1:20 (w/v). After the hydrolysis, the reaction was immediately terminated with 10 times of deionized water by volume. Then centrifugation was carried out to remove the sulfuric acid hydrolysate, and the centrifuged precipitate was redispersed into deionized water to obtain a suspension. A dialysis bag with the molecular weight cut-off of 8-14 kDa was filled with the suspension, and dialysis was repeated with deionized water until the pH of the suspension was stable, so as to obtain a cellulose nanocrystal suspension. The suspension was circulated 4 times at 10 MPa using a high-pressure homogenizer to obtain cellulose nanocrystals with a high aspect ratio of 51.

The cellulose crystal suspension was diluted to 0.4 wt %, and corn oil was added to the water phase according to the oil-water ratio of 8:2. Subsequently, high-speed shearing was carried out at 10000 rpm for 2 min using high-speed shearing equipment to obtain a coarse emulsion, and then the final Pickering emulsion was obtained. The viscosity of the emulsion was 25 Pa·s. The obtained emulsion remained stable after being placed at room temperature for 3 months.

Example 6 Preparation of Cellulose Nanocrystals with Low Aspect Ratio and Pickering Emulsion Crushed ginkgo seed shells were mixed with a preheated 4 wt % sodium hydroxide solution in a material-liquid ratio of 1:25 (w/v), and then the mixture was heated in a water bath at 90° C. for 2 h, filtered, washed with deionized water 4 times, and then dried with hot air at 50° C. The dried cellulose was mixed with a rinsing solution in a material-liquid ratio of 1:40 (w/v), and the mixture was heated in a water bath at 90° C. for 2 h. Then the mixture was filtered to remove the rinsing solution, and dried with hot air at 50° C.

The dry cellulose powder was mixed with a preheated sulfuric acid solution with the mass concentration of 62% for hydrolysis reaction, wherein the hydrolysis temperature was 45° C., the hydrolysis reaction time was 30 min, and the material-liquid ratio of the cellulose to the sulfuric acid solution was 1:15 (w/v). After the hydrolysis, the reaction was immediately terminated with 10 times of deionized water by volume. Then centrifugation was carried out to remove the sulfuric acid hydrolysate, and the centrifuged precipitate was redispersed into deionized water to obtain a suspension. A dialysis bag with the molecular weight cut-off of 8-14 kDa was filled with the suspension, and dialysis was repeated with deionized water until the pH of the suspension was stable, so as to obtain a cellulose nanocrystal suspension. The suspension was circulated 4 times at 70 MPa using a high-pressure homogenizer to obtain cellulose nanocrystals with a low aspect ratio of 8.

The cellulose crystal suspension was diluted to 0.1 wt %, and corn oil was added to the water phase according to the oil-water ratio of 1:9. Subsequently, high-speed shearing was carried out at 10000 rpm for 2 min using high-speed shearing equipment to obtain a coarse emulsion, and then the coarse emulsion was circulated 4 times at 10 MPa by a high-pressure homogenizer to obtain the final Pickering emulsion. The emulsion had the low viscosity of 0.05 Pa·s. The obtained emulsion remained stable after being placed at room temperature for 3 months.

Example 7 Stability of Emulsion in Different Environments

The emulsion obtained in Example 5 was placed in different environments to test the stability of the emulsion. A certain volume of freshly prepared emulsion was taken and diluted with the same volume of solutions with different pH values. The oil phase of the final emulsion reached 25%, and the pH of the diluted solution was in a range of 2.5-9.5. A certain volume of freshly prepared emulsion was taken and diluted with the same volume of solutions with different ion concentrations. The oil phase of the final emulsion reached 25%, and the ion concentration of the diluted solution was in a range of 10-100 mM. After the emulsion was diluted, the emulsion was placed at room temperature for 1 day, and no demulsification phenomenon occurred. In addition, after the fresh emulsion was heated to 90° C. in a water bath and insulated for 30 min, the emulsion did not demulsify.

Example 8 Preparation of Oil Gel Using CNCs with High Aspect Ratio

The CNCs with high aspect ratio obtained in Example 5 were taken and diluted to 0.4%. A water phase and an oil phase were mixed according to the oil-water ratio of 8:2. Subsequently, high-speed shearing was carried out at 10000 rpm for 2 min using high-speed shearing equipment to obtain an emulsion. The emulsion was dried to prepare an oil gel, which can be used in salad dressing, mayonnaise and the like, and the oil gel can replace partial hydrogenated vegetable oil to be applied in food.

Preparation of Ice Cream with the Oil Gel:
Formulas of the Ice Cream:
  Formula 1: 12% skimmed milk powder, 13% white granulated sugar, 5% cream, 0.2% gelatin, 10% egg yolk, and the rest of purified water.
  Formula 2: 12% skimmed milk powder, 13% white granulated sugar, 2% oil gel, 3% cream, 0.2% gelatin, 10% egg yolk, and the rest of purified water.

The preparation methods of the ice cream of the two formulas are the same. The preparation process of the ice cream is: mixing of raw and auxiliary materials, dissolving (40-50° C.), pasteurization (80° C., 15 min), homogenization (60-70° C., pressure 10-25 MPa), aging (2-4° C., 5 h), freezing (−4° C.), molding and packaging, hardening (−8° C., 6 h), refrigerating and finished product.

The expansion rate and melting rate of the ice cream prepared by formula 1 and formula 2 were tested. The method for determining the expansion rate of the ice cream is: before and after freezing, the same volume of mixture liquid and ice cream are taken, and the expansion rate of the ice cream is calculated by weighing. The method for determining the melting rate of the ice cream is as follows: a certain amount of hardened ice cream product is weighed and placed on a metal net in a constant temperature incubator at 35° C., a watch glass is placed under the metal net to hold the melt, and the mass of the melt is weighed after 30 min. The lower the melting rate, the better the melting resistance.

Expansion rate (%)=(The mass of the mixture liquid before freezing−The mass of the mixture liquid after freezing)/The mass of the same volume of ice cream after freezing*100

Melting rate (%)=(The mass of melted ice cream/The mass of ice cream before melting)*100

Experiments found that the ice cream prepared by using the oil gel has similar mouthfeel and texture to the ice cream prepared by using cream. The expansion rate and melting rate of the ice cream were measured. In the present example, the ice cream prepared by formula 2 and the ice cream prepared by formula 1 have similar expansion rates, both are 60-65%. However, after the oil gel was added to formula 2, the melting rate of the ice cream decreased significantly, and dropped to 18% from the melting rate of the ice cream prepared from formula 1 of 30%. This shows that the addition of the oil gel can significantly improve the melting resistance of ice cream.

Example 9 Preparation of Coated Flexible Packaging Materials Using CNCs with Low Aspect Ratio and Application Thereof for Preservation of Fruits and Vegetables The cellulose nanocrystals with low aspect ratio prepared in Example 6 were taken, and the surfaces of polypropylene films were uniformly coated with the CNCs with the concentration of 0.3 wt %-1.5 wt % by a coating machine. Then, the film was dried using constant temperature air at 25° C., and the film was placed in a constant temperature and constant humidity environment overnight for later use.

Apples of the same size without mechanical damage were chosen. After the apples were peeled, the apples were washed with sterile water, cut into pieces of uniform size, and drained. 80 g of apples was taken and wrapped in the uncoated film and the coated film respectively, and vacuumized. Then the apples were placed in a 4° C. freezer for 7 days, and then the total acid, vitamin C, soluble solids and color difference of the apples were measured. Among them, the total acid content was measured by the GB/T12456-2008 method, the color difference of the apples was measured by the UltraScan Pro1166 color difference meter, the vitamin C content was determined by GB5009.86-2016, and the soluble solids was tested by the Abbe refractometer.

The test results show that the quality of the apples packaged with the coated film is significantly higher than that of the apples packaged with the uncoated film. Among them, the brightness (L value) of the apples packaged with the coated film is 60.2, and the L value of the apples packaged with the uncoated film is 53.7. Compared with the brightness of fresh-cut apples (65.5), the brightness of the apples packaged with the uncoated film was reduced by 18%, and the browning degree of the apples packaged with the coated film was lighter. In addition, the nutrient content of the apples packaged with the coated film was better preserved. Compared with the apples packaged with the uncoated film, the titratable acid of the apples packaged with the coated film was increased by 0.98 time, the vitamin C content was increased by 46%, and the soluble solids was increased by 32%. It shows that the film coated by the CNCs with low aspect ratio can enhance the oxygen barrier effect of the original substrate, and thereby prolonging the shelf life of oxygen-sensitive foods.

Example 10 Preparation of Pickering Emulsion with Low Viscosity and High Fluidity Using CNCs with Low Aspect Ratio Curcumin was dissolved in an oil phase. The CNCs with low aspect ratio obtained in the Example 6 were diluted to 0.3 wt %, and an emulsion was prepared according to the oil-water ratio of 1:9. Subsequently, high-speed shearing was carried out at 10000 rpm for 2 min using high-speed shearing equipment to obtain a coarse emulsion, and then the coarse emulsion was circulated 4 times at 30 MPa using a high-pressure homogenizer to obtain the final Pickering emulsion. Determination of degradation rate of curcumin: a certain volume of emulsion was taken; the emulsion was mixed with ethanol in a ratio of 1:1; the mixture was centrifuged at 11000 rpm for 5 min; the supernatant was collected; and the absorbance at 426 nm was measured. Formula of degradation rate: Degradation rate $(100\%)=m_1/m_2 \times 100$, wherein $m_1$ is the mass of curcumin after the emulsion is placed, and $m_2$ is the mass of curcumin before the emulsion is placed.

The experiment found that the emulsion can protect curcumin well. After storage at room temperature for 7 days, the degradation rate of curcumin in the aqueous solution was 80%, while the degradation rate of curcumin in the emulsion was 44%, so that the bioavailability of curcumin, a water-insoluble substance, in plasma and tissues was improved.

Example 11 Preparation of Nano-Hydrogel Microbeads Using CNCs with Low Aspect Ratio The cellulose nanocrystals prepared in Example 6 were used as a substrate and mixed with sodium alginate and $Fe^{3+}$ to prepare magnetic nanohydrogel beads to be used in a drug delivery system, and sodium alginate beads were used as a control. The preparation process of the hydrogel beads was as follows: first, a certain volume of CNCs suspension was added to deoxygenated water, and the mixture was stirred for 15 min and then blown with nitrogen for 30 min. Then a certain amount of ferric chloride and ferric sulfate were added, and the mixture was stirred to dissolve at 60° C. Subsequently, 1.5 M sodium hydroxide was added dropwise, and then the mixture was centrifuged to obtain a precipitate. The precipitate was freeze-dried. A drug, such as ibuprofen, was added to a 4% sodium alginate solution. Then an appropriate amount of the freeze-dried precipitate was taken and added to the sodium alginate solution, and the mixed solution was stirred well. Subsequently, the solution was slowly added to a potassium chloride solution to carry out gelation treatment at a constant flow, and then the solution was centrifuged to obtain drug-embedded hydrogel beads. By measuring the physical and mechanical properties of the microbeads, as well as the drug release rate, it can be seen that the mechanical strength of the microbeads added with the cellulose nanocrystals was significantly improved, the microbeads were not easily damaged by acid and alkaline environments, and the drug release rate was reduced. Because the entangled structure of cellulose plays a role in limiting the diffusion of drugs, when the release time was 150 min, the drug release rate of the microbeads added with the cellulose nanocrystals was 25% lower than that of the microbeads without the cellulose nanocrystals added. In the entire drug release process, the microbeads added with the cellulose nanocrystals showed a relatively uniform drug release process.

The method for determining the drug release rate in vitro is as follows: 0.1 g of microbeads are accurately weighed and placed in a certain volume of 0.01 M phosphate buffer (pH=7.4). Then the system is maintained at 37° C. and stirred continuously at 100 rpm. Then 1 mL of sample is pipetted at the set time point for carrying out UV spectrophotometer measurement ($\lambda=222$ nm).

What is claimed is:

1. A method for preparing a Pickering emulsion using cellulose from ginkgo seed shells, comprising the following steps:
   (1) purifying cellulose from ginkgo seed shells: mixing crushed ginkgo seed shells with a preheated 2-5 wt % sodium hydroxide solution in a material-liquid ratio of 1:20 to 1:40 (w/v); then heating the mixture in a water bath at 80-100° C. for 1-3 h; carrying out filtering and washing with deionized water 2-4 times; then carrying out drying with hot air at 40-60° C. to obtain a dried cellulose; mixing the dried cellulose with a rinsing solution in a material-liquid ratio of 1:20 to 1:50 (w/v); heating the mixture in a water bath at 80-100° C. for 1-3 h; then filtering the mixture to remove the rinsing solution; and carrying out drying with hot air at 40-60° C. to obtain dried cellulose powder;
   (2) preparing cellulose nanocrystals (CNCs): mixing the dried cellulose powder obtained in step (1) with a preheated sulfuric acid solution with a mass concentration of 58-64% for carrying out a hydrolysis reaction, wherein a hydrolysis temperature is 40-50° C., the hydrolysis reaction time is 10-60 min, and a material-liquid ratio of the cellulose to the sulfuric acid solution is 1:10 to 1:20 (w/v); after the hydrolysis, immediately terminating the hydrolysis reaction with 10-15 times of deionized water by volume; then carrying out centrifugation to remove a sulfuric acid hydrolysate; redispersing centrifuged precipitate into deionized water to obtain a suspension; filling a dialysis bag with the suspension; and repeating dialysis with deionized water until a pH value of the suspension is stable to obtain a cellulose microcrystal suspension;
   (3) preparing cellulose nanocrystals with different aspect ratios: homogenizing the cellulose suspension obtained in step (2), wherein a homogenization pressure is 10-100 MPa, the number of cycles is 4, and a homogenization temperature is room temperature; cellulose nanocrystals with high aspect ratios are obtained by homogenization treatment at a pressure of 10-30 MPa; and cellulose nanocrystals with low aspect ratios are obtained by homogenization treatment at a pressure of 30-100 MPa; and (4) preparing the Pickering emulsion: mixing the cellulose nanocrystals in step (3) used as a solid particle emulsifier with an oil phase, and carrying out emulsification to obtain the Pickering emulsion.

2. The method of claim 1, wherein in step (4), the cellulose nanocrystals with high aspect ratios are mixed with 50%-80% of an oil phase, and emulsification is carried out to obtain a Pickering emulsion with a high oil phase and high viscosity; or the cellulose nanocrystals with low aspect ratios are mixed with 10%-50% of an oil phase, and emulsification is carried out to obtain a Pickering emulsion with low viscosity and high fluidity.

3. The Pickering emulsion prepared by the method of claim 1, wherein the Pickering emulsion is stabilized by cellulose from ginkgo seed shells.

4. The Pickering emulsion prepared by the method of claim 2, wherein the Pickering emulsion is stabilized by cellulose from ginkgo seed shells.

5. A method of preparing a Pickering emulsion, comprising the following steps:
(1) treating crushed ginkgo seed shells with a hot alkali solution, then carrying out rinsing with a rinsing solution, and carrying out drying with hot air to obtain high-purity cellulose from ginkgo seed shells;
(2) hydrolyzing the cellulose from ginkgo seed shells obtained in step (1) with sulfuric acid; after the hydrolysis, adding deionized water immediately to terminate a hydrolysis reaction; centrifuging a hydrolysate to obtain a precipitate; dialyzing the precipitate with deionized water to remove inorganic salt ions; and obtaining a cellulose microcrystal suspension after dialysis;
(3) homogenizing the cellulose suspension obtained in step (2), and preparing cellulose nanocrystals (CNCs) with different aspect ratios by adjusting a homogenization pressure; and
(4) using the cellulose nanocrystals in step (3) as a solid particle emulsifier, diluting the cellulose nanocrystals with deionized water to serve as a water phase, mixing the water phase with an oil phase, and carrying out emulsification to obtain the Pickering emulsion.

6. The method of claim 5, wherein the rinsing solution in step (1) contains 1.5-2.0 g of sodium chlorite, 2.5-3.0 g of sodium hydroxide and 7-8 mL of glacial acetic acid for each 100 mL.

7. The method of claim 5, wherein in step (2), a mass concentration of the sulfuric acid solution used for sulfuric acid washing is 58-64%, a hydrolysis temperature is 40-50° C., the hydrolysis reaction time is 10-60 min, and a material-liquid ratio of the cellulose to the sulfuric acid solution is 1:10 to 1:20 (w/v).

8. The method of claim 5, wherein conditions for preparing the cellulose nanocrystals with different aspect ratios in step (3) are as follows: a homogenization pressure is 10-100 MPa, the number of cycles is 4, and a homogenization temperature is 25° C.; CNCs with high aspect ratios are obtained by homogenization treatment under a pressure of 10-30 MPa; and CNCs with low aspect ratios are obtained by homogenization treatment under a pressure of 30-100 MPa.

9. The method of claim 5, wherein in step (4), a concentration of the cellulose nanocrystals in the water phase is 0.10-0.50 wt %.

10. The method of claim 5, wherein the oil phase in step (4) comprises corn oil, soybean oil and peanut oil.

11. The method of claim 5, wherein the emulsification in step (4) is carried out by adopting a high-speed shearing process or a homogenization process or a combination of the two processes to prepare the Pickering emulsion, wherein conditions for the high-speed shearing process are as follows: a shearing rate is 8000-10000 rpm, and the shearing time is 1-3 min; and conditions for the high-pressure homogenization process are as follows: a homogenization pressure is 10-30 MPa, and the number of cycles is 2-4.

12. The Pickering emulsion prepared by the method of claim 5, wherein the Pickering emulsion is stabilized by cellulose from ginkgo seed shells.

13. The Pickering emulsion prepared by the method of claim 6, wherein the Pickering emulsion is stabilized by cellulose from ginkgo seed shells.

14. The Pickering emulsion prepared by the method of claim 7, wherein the Pickering emulsion is stabilized by cellulose from ginkgo seed shells.

15. The Pickering emulsion prepared by the method of claim 8, wherein the Pickering emulsion is stabilized by cellulose from ginkgo seed shells.

16. The Pickering emulsion prepared by the method of claim 9, wherein the Pickering emulsion is stabilized by cellulose from ginkgo seed shells.

17. The Pickering emulsion prepared by the method of claim 10, wherein the Pickering emulsion is stabilized by cellulose from ginkgo seed shells.

18. The Pickering emulsion prepared by the method of claim 11, wherein the Pickering emulsion is stabilized by cellulose from ginkgo seed shells.

\* \* \* \* \*